United States Patent [19]
Webster, Jr.

[11] Patent Number: 5,893,885
[45] Date of Patent: Apr. 13, 1999

[54] MULTI-ELECTRODE ABLATION CATHETER

[75] Inventor: Wilton W. Webster, Jr., Baldwin Park, Calif.

[73] Assignee: Cordis Webster, Inc., Baldwin Park, Calif.

[21] Appl. No.: 08/742,352

[22] Filed: Nov. 1, 1996

[51] Int. Cl.$^6$ ............................................. A61B 17/36
[52] U.S. Cl. .................... 607/122; 606/41; 606/31; 607/102
[58] Field of Search .................... 606/31, 41, 42, 606/45–50; 600/372–374; 607/100–102, 122

[56] References Cited

U.S. PATENT DOCUMENTS

| | | |
|---|---|---|
| 4,411,266 | 10/1983 | Cosman .................... 606/49 |
| 4,960,134 | 10/1990 | Webster, Jr. . |
| 4,966,597 | 10/1990 | Cosman .................... 606/50 |
| 5,327,905 | 7/1994 | Avitall .................... 606/45 |
| 5,529,067 | 6/1996 | Larsen et al. .................... 606/41 |

*Primary Examiner*—Michael Peffley
*Attorney, Agent, or Firm*—Christie, Parker & Hale, LLP

[57] ABSTRACT

A multi-electrode ablation catheter comprises a plurality of thick-walled gold alloy electrodes mounted on the tip section of an elongated electrophysiology catheter. Each electrode is electrically connected to a switching unit by leads comprising paired copper and constantan wires. The switching unit is electrically connected to an RF generator, a temperature monitor and an ECG monitor. The switching unit enables an operator to switch between a first mode for monitoring ECG and a second mode for delivering RF energy for tissue ablation to a selected electrode and monitoring the temperature of that electrode. The copper wire of the lead delivers RF energy and the copper wire and constantan wire combine to form a thermocouple for temperature monitoring.

24 Claims, 7 Drawing Sheets

MULTI-ELECTRODE ABLATION CATHETER

FIELD OF THE INVENTION

The present invention generally relates to electrode catheters useful for treating arrhythmias in the heart.

BACKGROUND OF THE INVENTION

Radio frequency catheter ablation in the heart is now well known. In this therapy small lesions are formed that interrupt pathways of muscular excitation and terminate certain arrhythmias. There are some specialized applications where larger or longer lesions are necessary to achieve a successful therapy. As an example, there is a need for one or more such lesions to terminate atrial flutter and atrial fibrillation. In these cases, the lesions need to exceed one centimeter in length and be uninterrupted.

One method of producing such a lesion is to drag a tip electrode, preferably with a thermocouple attached along the surface of an atrium while applying RF energy. The thermocouple allows the operator of the catheter to measure the temperature in the tip electrode to ensure good ablation of the heart tissue. However, in the beating heart, the tip electrode may hop or swerve sideways, especially in trabeculated areas, producing intermittent lesions.

Another method of producing lesions longer than one centimeter in length without gaps is by using a long spiral electrode that wraps around the catheter body multiple times. This creates multiple lesions which overlap, thus creating a continuous long lesion. However, a spiral electrode has the disadvantage of producing poor electrocardiograms due to its length. It is also difficult to measure temperature that is representative of the ablation site.

Several practitioners in the field of electrophysiology and especially RF ablation of atrial arrhythmias have suggested the use of multiple, preferably ten, spaced-apart ring electrodes. Such a catheter, however, is difficult to construct for several reasons. For example, soft copper lead wires are typically used to connect the ring electrodes with a high frequency generator to create the radio frequency ablation at the ring electrodes. Soft copper is needed to deliver the RF energy and allow a cost effective catheter design. However, a RF ablation catheter has to be relatively small, about 8 French, for placement inside the heart. The inner diameter of the catheter is even smaller and restricts the number of wires that can be placed in the catheter. Therefore, the copper wire must be large enough to carry at least one ampere of current, yet small enough to fit within the catheter. Very small diameter copper wires, e.g., No. 40 copper wires, would be ideal for use in a 10 electrode ablation catheter, but are too fragile to allow for manipulation and catheter construction. Hence, it is difficult to get enough copper lead wires, e.g., 20 (10 lead wires for the electrodes and 10 lead wires for temperature sensors), to the electrodes which have a large enough diameter to carry the required current, e.g., 1 ampere.

Moreover, electrophysiology catheters typically have nearly flush platinum or platinum/iridium electrodes which are less thrombogenic and traumatic. Where there is a congested arrangement of elements within the tip cross section so that these flush rings cannot be buried within the tip, the ring electrodes are typically thin, usually about 0.003 inch. These rings must be galvanically stable, biocompatible and extremely strong so that they do not break and fall off the tip and be left in the patient. Thin platinum iridium rings are typically chosen. However, thin platinum iridium rings have very poor circumferential heat transfer. Hence, they are not compatible with a single thermocouple design for predicting the temperature at all points along the ring except for the area directly over the thermocouple.

Accordingly, there is a need for a catheter construction which allows for multiple site ablation with accurate temperature monitoring means while still maintaining a small overall catheter diameter.

SUMMARY OF THE INVENTION

The present invention provides a multi-electrode, preferably deflectable, ablation catheter for making long lesions within the heart. The catheter comprises multiple spaced-apart electrodes. Each electrode is connected to a lead comprising a first wire of a first highly conductive material, e.g., copper and stainless steel with a silver core or the like which is paired with and enameled to a second wire of high strength material different from the first material, preferably constantan. The high strength wire supports and allows the use of a very small diameter highly conductive wire, e.g., copper wire. Further, the combination of first and second materials, e.g., copper and constantan, act as a thermocouple for monitoring the temperature at each electrode. The catheter is connected to an ECG monitor, a source of RF energy and a temperature monitoring means through a switching control unit that allows the operator to switch from monitoring the ECG of a patient to delivering RF energy for ablation to a selected electrode and simultaneously monitoring the temperature of that selected electrode.

BRIEF DESCRIPTION OF THE DRAWINGS

Reference is now made to the following figures where similar reference numerals depict similar components in the several views, and where.

DETAILED DESCRIPTION

Figure 1:
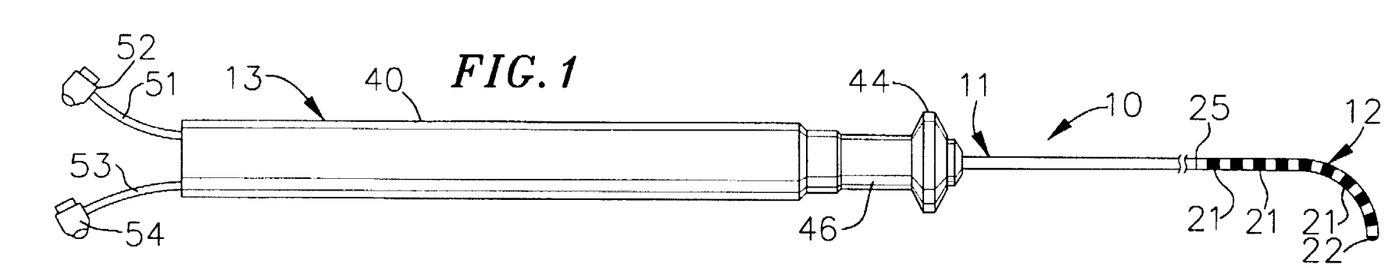
FIG. 1 is a plan view of a multi-electrode ablation catheter of the present invention.

With reference to FIG. 1, there is shown a preferred multi-electrode ablation catheter 10 constructed in accordance with the present invention. The multi-electrode ablation catheter comprises an elongated catheter body 11 having proximal and distal ends, a flexible catheter tip section 12 at the distal end of the catheter body 11, and a control handle 13 at the proximal end of the catheter body.

Figure 2:
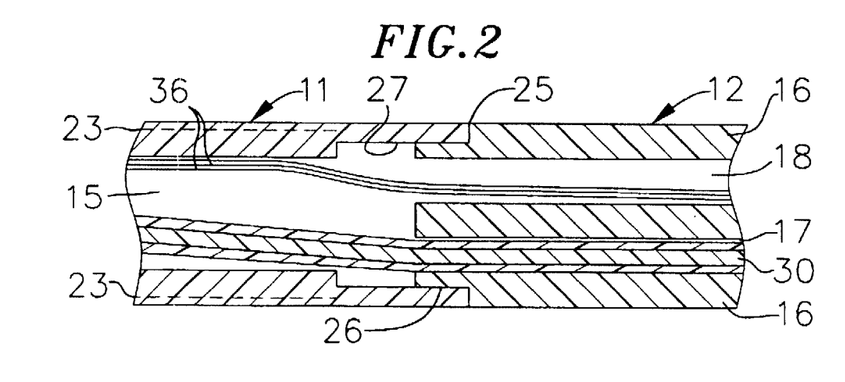
FIG. 2 is a cross sectional view of the catheter of the present invention taken along the junction of the proximal catheter body and the flexible distal catheter section.
Figure 8:
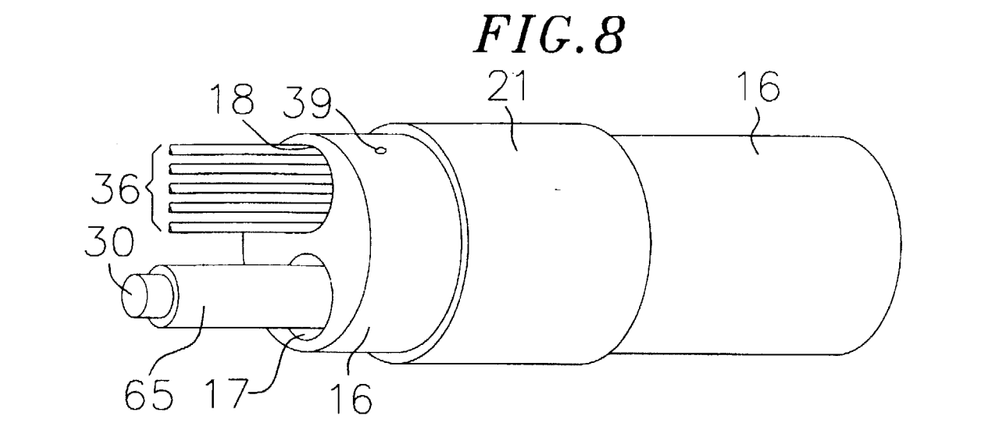
FIG. 8 is a cut away perspective view of showing a preferred method of electrode-lead attachment.

The catheter body 11 can have a single lumen, such as illustrated in FIG. 2 and described in U.S. Pat. No. Re. 34,502 issued Jan. 11, 1994, the disclosure of which is hereby incorporated by reference; or multiple lumens, such as illustrated in FIG. 8 and described in U.S. Pat. No. 5,431,168, issued Jul. 11, 1995, the disclosure of which is hereby incorporated by reference.

With reference to FIGS. 2–8, the catheter body 11 comprises an elongate tubular construction having a single lumen 15. The catheter body is flexible, i.e. bendable, but is substantially non-compressible along its length. The catheter body may be of any suitable construction and made out of any suitable material. A presently preferred construction comprises polyurethane reinforced with a braided stainless steel mesh 23.

The overall length and diameter of the catheter may vary according to the application. A presently preferred catheter has a length of about 48 inches, an outer diameter of about 0.09 inches, and an inner diameter of the catheter body of about 0.04 inches.

The catheter tip section 12 comprises a short section of flexible tubing 16 having a pair of nonoverlapping, e.g. side-by-side, first and second lumens 17 and 18 which are off axis, i.e not coaxial with the catheter tip section 12. The tubing is made of any suitable material and is preferably more flexible than the catheter body. A presently preferred material for the catheter tip section is polyurethane that is not reinforced with a metallic braid.

The diameter of the catheter tip section 12 is preferably the same as or slightly smaller than the catheter body. In a preferred embodiment the diameter of the catheter body is about 0.08 inches. The length of the catheter tip section can also vary as desired, but is preferably about three inches long.

A preferred means for attaching the catheter tip section 12 to the catheter body 11 is illustrated in FIG. 2. The proximal end of the catheter tip section 12 comprises an outer circumferential notch 26 and the distal end of the catheter body 11 comprises an inner circumferential notch 27. The notches are sized such that the proximal end of the catheter tip section 12 fits snugly into the distal end of the catheter body 11. The catheter tip section 12 is then fixedly attached to the catheter body 11 by polyurethane or the like, creating a seam 25 on the outer surface of the catheter at the junction between the catheter tip section 12 and the catheter body 11. As shown, the lumen 15 of the catheter body 11 is in communication with both lumens 17 and 18 of the catheter tip section 12.

Along the length of the catheter tip section 12 are a plurality of ring electrodes 21. The length of the electrodes is not critical, but is preferably about 4 mm. The electrodes are spaced apart a distance of about 2 to 4 mm and preferably about 3 to 4 mm. Less than about 2 mm spacing makes the catheter tip section too stiff. A spacing greater than about 5 mm makes it difficult to achieve overlap in lesions. A spacing of about 3 to 4 mm between the electrodes provides the most preferred combination of tip flexibility and lesions overlap thus allowing the creation of a long continuous lesion.

Figure 4:
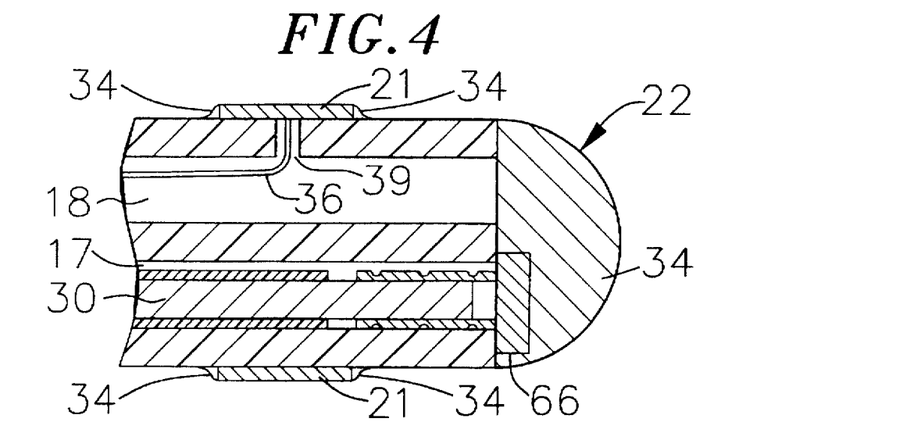
FIG. 4 is a cross sectional view of a catheter tip section of one embodiment of the invention.

The electrodes are constructed out of an electrically and thermally conductive material, preferably a gold alloy and more preferably a gold alloy. A gold alloy comprises about 90% gold and about 10% platinum is presently preferred due to its commercial availability. The electrodes 21 are galvanically stable and biocompatible. The electrodes are relatively thick, preferably about 0.008 inches and have the same or slightly smaller inner diameter as the outer diameter of the catheter tip. As illustrated in FIG. 4, the electrodes protrude from the surface of the catheter tip.

Figure 3:
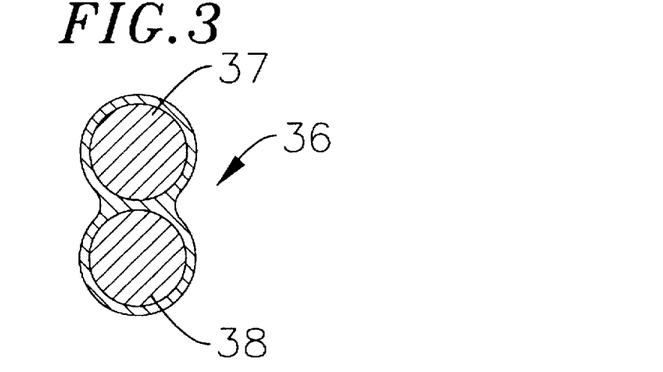
FIG. 3 is a cross section of a lead wire of the present invention.

Each electrode is connected to a separate lead 36. As illustrated in FIG. 3, the leads 36 comprise two wires enameled together. Wire 37 is a number 40 copper wire and wire 38 is a number 40 constantan wire. In this configuration the constantan wire 38, which has high strength, supports the copper wire 37, which is soft and fragile. This allows the catheter to have up to ten or more electrodes each individually connected with up to ten or more leads. Because the leads 36 are constructed out of the two different types of wire, the leads 36 also serve as a thermocouple for measuring the temperature at electrode 21.

The leads 36 extend through lumen 15 of the catheter and into lumen 18 of the catheter tip section 12. The leads 36 also extend through the handle and are then segregated into copper wires and constantan wires as detailed below.

Referring to FIGS. 4 and 8, a small hole 39 is made on the side of the catheter tip near the lumen. Such a hole may be created, for example, by inserting a needle through the tip section wall and heating the needle sufficiently to form a permanent hole. A lead 36 is then drawn through the hole 39 by using a microhook or the like. The ends of the copper and constantan (wires 37 and 38) are stripped of their enamel coating and are then soldered or welded to the underside of the electrode 21. The electrode is then slid into position over the hole 39 and fixed in place with polyurethane 34. In the embodiment illustrated, the electrode is not set within the wall of the catheter tip section 12 but actually protrudes from the surface of the wall of the catheter tip section 12.

Gold alloy electrodes 21 are preferred as they provide sufficient thermal conductivity so that the temperature at the side of the electrode opposite ablation site, i.e., the side in contact with the heart tissue during ablation, is within a few degrees of the temperature at the ablation site. Accordingly, the location of the thermocouple, i.e., the location where the leads 36 are welded to the electrodes, is not critical and a location adjacent lumen 18, as shown in FIG. 4 is presently preferred.

In some situations, however, it is important to monitor the temperature at the ablation site more accurately. In an application wherein the catheter tip section 12 is deflected, forming a curve, and the electrodes make contact against the heart tissue along the outside of the curve, the lead attachment described above is preferred. However, in those applications where the site of contact between the electrodes and the heart tissue is along the inside of the curve, i.e., adjacent the puller wire, it is preferred that the thermocouples, i.e., the location of the connection of the leads to the electrodes, be located along the inside of the curve.

Figure 5:
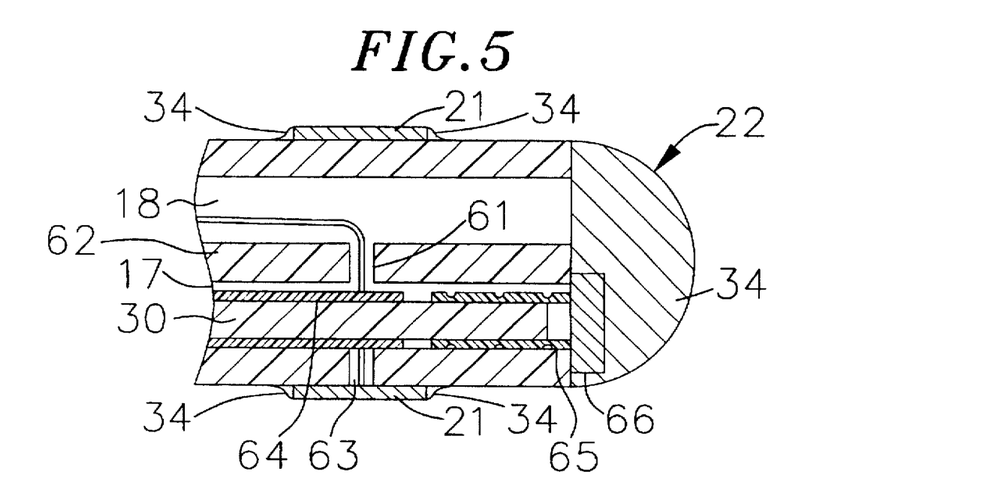
FIG. 5 is a cross sectional view of a catheter tip section of another embodiment of the invention.

The alternate embodiment of the invention shown in FIG. 5 illustrates such an arrangement. As shown, the leads 36 in lumen 18 pass through a hole 61 in the septum 62 separating lumens 17 and 18, extend around the puller wire 30 and across lumen 17 and then through hole 63 to the electrode 21. To make such a construction, holes 61 and 63 are first created, for example, by inserting a needle through the catheter tip wall, across the lumen 17 (before the puller wire 30 is positioned therein) and septum and then heating the needle sufficiently to fix the holes 61 and 63.

The leads 36 are then positioned in lumen 18 and a microhook is inserted through holes 61 and 63 to snag one of the leads 36. Once snagged, the microhook is withdrawn, drawing the lead out through the holes 61 and 63. The ends of the copper and constantan wires 37 and 38 are then stripped and soldered or welded to the electrode 21 as described above. Once all of the leads 36 are attached to the electrodes 21, the puller wire 30 is inserted into lumen 17 and anchored to the catheter tip section 12 as described below. The portions of the leads 36 which extend across lumen 17 lie between a Teflon® sheath 64 surrounding the puller wire 30 and the wall of the catheter tip section 12 forming the lumen 17.

Figure 6:
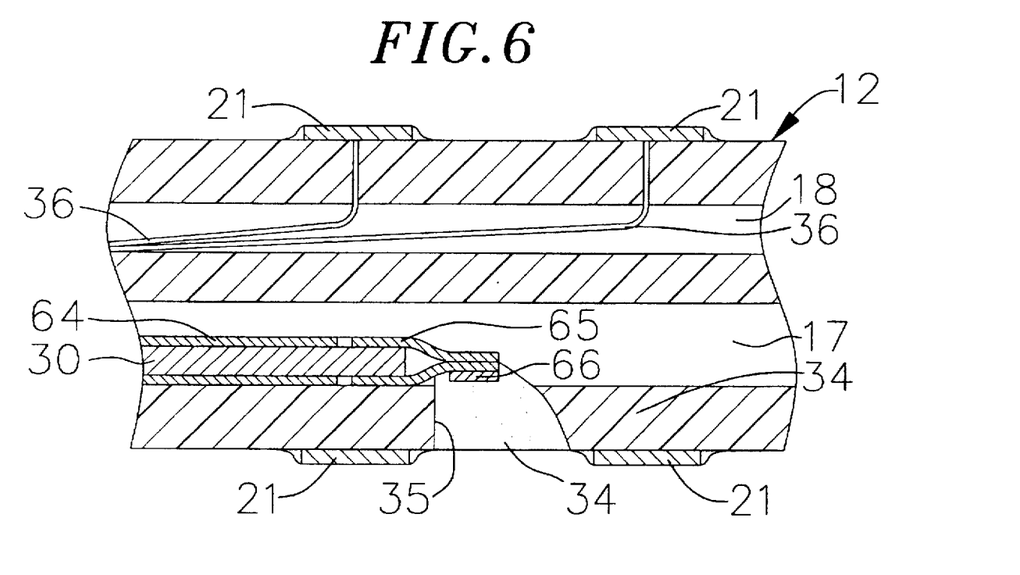
FIG. 6 is a cross sectional view of a portion of the catheter tip section showing one means for attaching the puller wire.
Figure 7A:
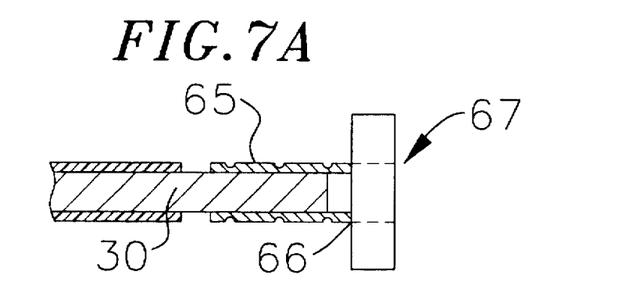
FIGS. 7a and 7b are top and side cross sectional views of a preferred puller wire anchor.
Figure 7B:
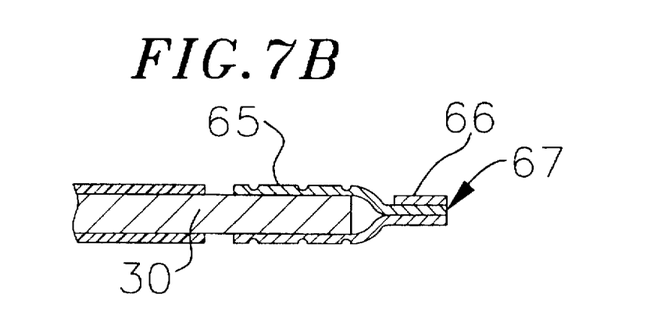

FIGS. 6, 7a and 7b depicts a preferred means for fastening a puller wire 30 to the side of the catheter tip section 12. The puller wire 30 extends through a Teflon® sheath 64 to prevent it from cutting into the wall of the catheter body and tip section. At the distal end of the puller wire 30 the Teflon sheath 64 is removed and a metal tube 65, e.g., a short segment of hypodermic stock, is fixedly attached, e.g., by crimping, to the puller wire 30. The tube 65 has a section which extends a short distance beyond the end of the puller wire 30. A small section of stainless steel ribbon 66 or the like is soldered or welded in a transverse arrangement to the tube section extending beyond the puller wire which is flattened during the operation. This creates a T-bar or anchor 67. A notch 35 is created in the side of the catheter tip section 12 resulting in an opening into lumen 17. The anchor 67 lies within the notch 35. Because the length of the ribbon 66 is longer than the diameter of the opening into lumen 17, the anchor 67 cannot be pulled into the lumen 17. The notch is then sealed with polyurethane 34 to give a smooth surface.

In an alternate embodiment, as shown in FIG. 4, the puller wire 30 extends to the distal end of the lumen 17 with the anchor 67, which is attached to the end of the puller wire 30 lying beyond the end of the lumen 18. The anchor 67 is fixed in this position by a polyurethane cap 34 which also seals the distal end of the catheter tip section 12. Because the ribbon 66 is longer than the diameter of the lumen 17, the anchor 67 cannot be pulled back into the lumen 17 when the tip section 12 is deflected.

The puller wire 30 is controlled by the control handle 13. The control handle 13 is described in detail in U.S. Pat. No. Re. 34,502, the disclosure of which is incorporated by reference. Briefly, the proximal end of the puller wire is fixed within the handle body 40 of the control handle. The proximal end of the catheter body is fixed to the movable piston 46 and thumb rest 44. As the operator translates the piston and thumb rest away from the handle body, the puller wire is translated within the catheter. Because the catheter body is not compressible, only the flexible distal tip bends. The bend will be concave along the lumen 17 containing the puller wire. Thus, the catheter tip becomes steerable due to the translation of the piston in the control handle. If the puller wire is connected to the side of the catheter tip, (see FIG. 6) then the catheter tip will only become concave up to the point of attachment of the puller wire. If the puller wire is attached to the distal end of the catheter tip, (see FIG. 4), then the entire catheter tip will become concave.

Figure 9:
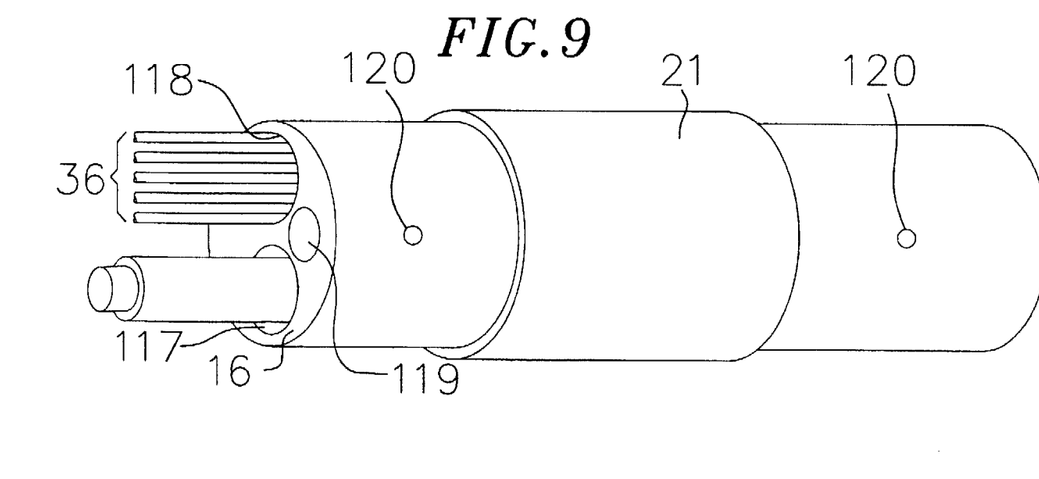
FIG. 9 is a cut away perspective view of an alternate embodiment of the present invention.

FIG. 9 illustrates yet another embodiment of the present invention. The catheter body and catheter tip in this embodiment all have three lumens, 117, 118 and 119. A catheter of this construction is fully described in U.S. Pat. No. 5,431, 168, issued Jul. 11, 1995, the disclosure of which is hereby incorporated by reference. In the catheter tip section, lumen 117 is analogous to lumen 17, is off axis from the catheter tip, and is the lumen for the puller wire. Lumen 118 is analogous to lumen 18, is also off axis and is the lumen for the lead wires. Lumen 119 is an irrigation lumen for providing cooling physiological solutions to the point of ablation to keep the electrodes cool. The irrigation is provided for by a plurality of holes 120 located between the electrodes 21. An irrigation side arm or conduit (not illustrated) is connected to the catheter body near the handle to provide an entry point for the irrigation fluid to lumen 119.

Figure 11:
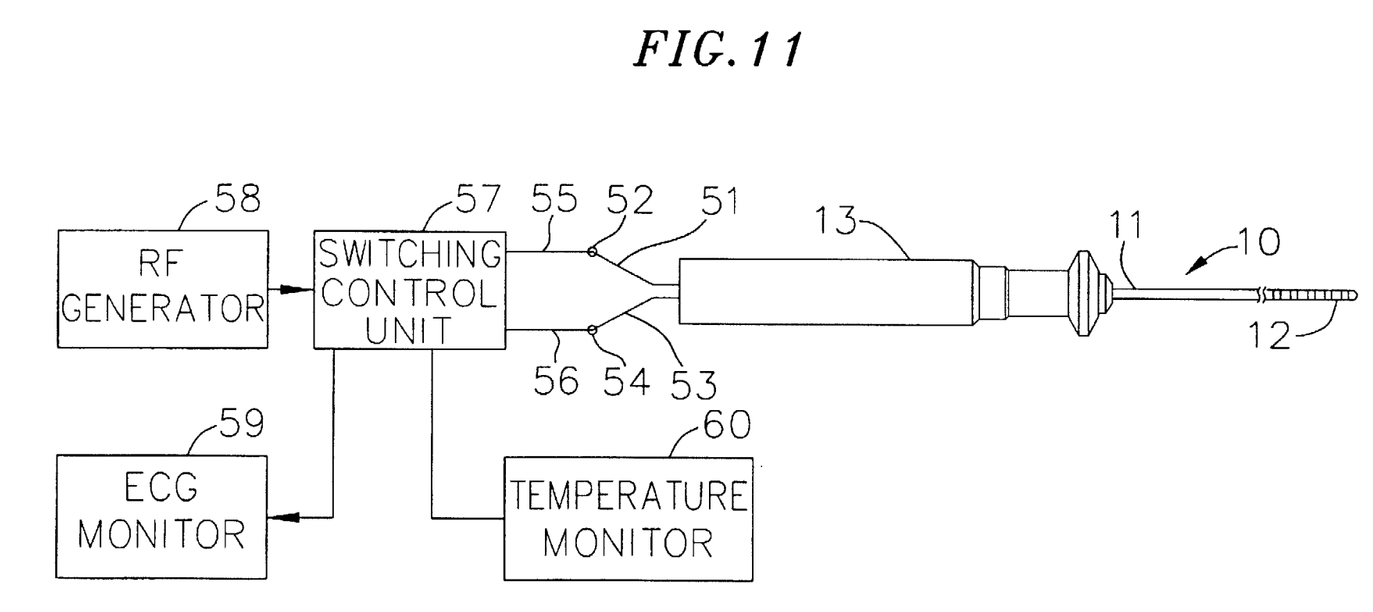
FIG. 11 is a schematic view of an RF generator, switching control unit, ECG monitor, and temperature monitor connected to the multi-electrode catheter of the present invention.

As shown in FIGS. 1 and 11, at the proximal end of the handle, there are two connection cables 51 and 53. Connection cable 51 contains the copper lead wires only, and connection cable 53 contain the constantan lead wires only. At the end of cable 51 is a connector 52 and at the end of the cable 53 is connector 54. These connectors are in turn connected to a switching control unit 57 via extension cables 55 and 56. Because the leads 36 connected to the electrodes 21 contain both copper and constantan wires, the leads 36 serve as a connection for RF energy (the copper wire) and as a thermocouple (both the copper wire and the constantan wire). The switching control unit 57 allows the operator to switch from monitoring the ECG of the patient to delivering RF energy to the electrodes and monitoring the temperature of the electrodes using the thermocouple.

Figure 10:
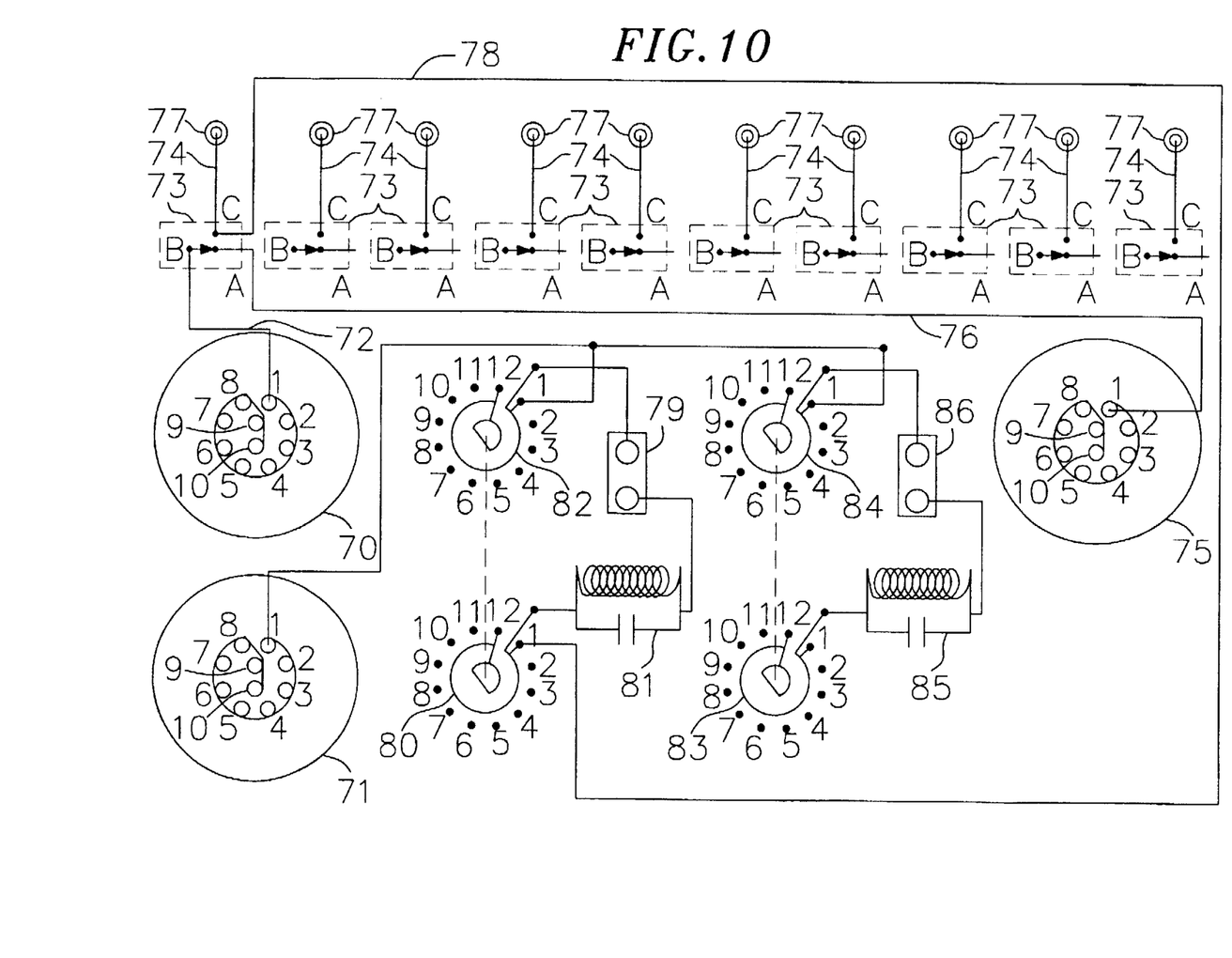
FIG. 10 is a schematic view of a switching control unit of the present invention.

FIG. 10 is a schematic of a preferred manually operated switching control unit 57 for up to a 10 electrode catheter. The switching unit 57 comprises a first multi-socket input jack 70 for receiving the multi-pin connector to which the copper lead wires are connected and a second multi-socket input jack 71 for receiving the multi-pin connector to which the constantan lead wires are connected. Each socket of the first jack 70 is connected by a wire 72 (only one wire 72 is shown) to a toggle switch 73. Accordingly, each toggle switch 73 is associated with a particular copper lead wire and hence to a particular catheter electrode 21. The toggle switch 73 has two positions, designated "A" and"C." The "A" position of each switch is connected via wires 76 (only one wire 76 is shown) to a multi-socket output jack 75 which receives the multi-pin connector of an ECG recorder. In this arrangement, when the toggle switch 73 is in the "A" position, the ECG recorder 59 receives electrical signals from the electrode associated with that toggle switch.

The "C" position of the toggle switch is connected to two things. First, it is connected via wire 74 to a single socket banana jack 77 which receives one of the two leads of an RF generator. Hence, there is one banana jack 77 associated with each catheter electrode 21. The second of the RF generator leads is connected, in unipolar operation, to a ground electrode, e.g., a back patch electrode, or, in bipolar operation, to the single socket banana jack 77 associated with another electrode 21.

In uni-polar operation, to ablate tissue adjacent a particular electrode 21, the toggle switch 73 associated with that electrode is put into the "C" position and one of the RF generator leads is plugged into the banana jack 77 associated with that toggle switch 73 and electrode 21. The other RF generator lead is connected to a back patch electrode or the like. When power is applied by the RF generator, current flows between the electrode and the back patch. Due to the electrical resistance of the heart tissue, heat is generated, forming a lesion at the site of the electrode. Power is thus applied in an amount and for a time to effect the desired amount of ablation, i.e., to create a lesion of desired size and depth.

To ablate tissue in the bipolar mode, the second RF generator lead is plugged into the banana jack 77 corresponding to a second electrode 21. When power is applied by the RF generator, current flows through the heart wall tissue between the first and second electrodes. Again, heat is generated due to the electrical resistance of the heart tissue and the lesion is formed beginning at the first electrode and extending toward the second electrode. If the second electrode is sufficiently close, the lesion extends completely between the two electrodes.

The C position of the toggle switch 73 is also connected by wire 78 (only one wire 78 is shown) to one socket of a two socket thermocouple connector 79 for receiving the two pin plug of a digital thermometer. The connection is made through a rotary switch 80 and RF filter 81. The rotary switch 80 has 10 positions which can be designated, each position connected to the C position of a particular toggle switch 73. The RF filter prevents ablation energy from passing to the digital thermometer.

The second socket of the two socket thermocouple connector 79 is connected to the constantan multiple socket jack 71 through rotary switch 82, which like rotary switch 80 has 10 positions. Each position of the rotary switch 82 is connected to a particular socket of the constantan jack 71. Rotary switches 80 and 82 are ganged together so that they can be dialed to the same position which corresponds to the electrode for which temperature monitoring is desired.

There is provided a second set of rotary switches 83 and 84, RF filter 85 and two socket thermocouple connector 86 which are connected to the constantan jack 71 and C positions of the toggle switches 73, as described above so that when the bipolar mode is used, the temperature of the second electrode can be measured as well as that of the first electrode. This is done by dialing the ganged switches 83 and 84 to the position corresponding to the second electrode and then reading the digital temperature readout of a second digital thermometer.

In use, the electrode catheter is positioned into the heart of a patient with the catheter tip section 12 usually placed within the right atrium, although other locations can be used as well. The switching unit 57 is set to allow for the monitoring of the ECG of the patient to locate areas for ablation. The catheter is then positioned over a site for ablation and switched to apply RF energy sequentially to each electrode, while monitoring the temperature of the ablating electrode. Long linear lesions are created due to the overlap in endomyocardial tissue death and the 3 to 4 mm spacing apart of each electrode pair. Once the ablation procedure is complete, the catheter is removed from the patient.

Figure 12:
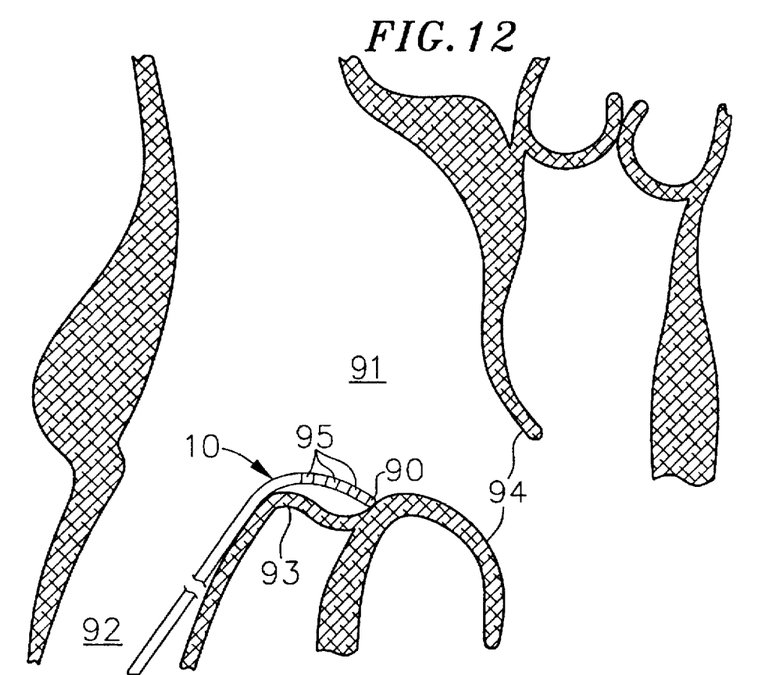
FIG. 12 is a cut away view showing the initial placement of the catheter in the right atrium in a preferred method according to the present invention.

The catheter of the present invention is particularly useful in creating linear lesions for correcting atrial flutter. With reference to FIG. 12, in such an embodiment, a deflectable multi-ablation catheter 10, e.g., as described above and comprising a tip electrode 90, is passed into the right atrium 91 through the inferior vena cava 92. Preferably, the tip electrode is a split tip electrode as described in pending U.S. patent application entitled Split Tip Electrode Catheter filed Oct. 4, 1996, naming Wilton W. Webster, Jr. as inventor and claiming priority to provisional application in Ser. No. 60/005,451 filed Oct. 6, 1995, which is incorporated by reference. The catheter tip section is deflected or curved over the ithsmus 93 between the inferior vena cava 92 and the tricuspid valve 94 as shown so that the tip electrode 90 of the catheter contacts the edge of the tricuspid valve 94.

Figure 13:
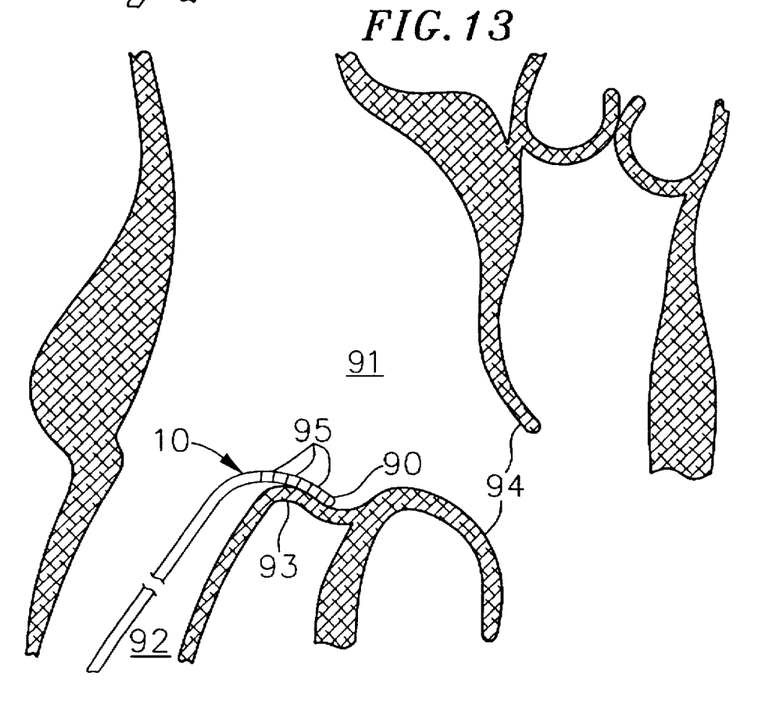
FIG. 13 is a cut away view showing a subsequent placement of the catheter in the right atrium in the method shown in FIG. 13.

While applying RF energy to the tip electrode 90, the tip section is then dragged back to the position shown in FIG. 13 so that ring electrodes 95 along the length of the catheter tip section contact the atrial wall. RF energy is then applied to the ring electrodes in sequence to complete the linear lesion between the tricuspid valve and the inferior vena cava. This linear lesion blocks the electrical wave of excitation which causes the atrial flutter allowing the atrium to resume normal beating.

Thus, a multi-electrode ablation catheter is disclosed which allows individual ablation control of each electrode and individual temperature monitoring of each electrode. Further, the use of paired copper and constantan lead wires reduces the need for more lead wires and/or larger diameter lead wires. This in turn allows for a smaller diameter catheter than would be otherwise necessary for the number of electrodes carried by the catheter. The reduction in the diameter of the catheter as provided by this invention enables the creation of thinner lesions in the heart with less destruction of heart tissue, which is a very desirable result.

While embodiments and applications of this invention have been illustrated and described, it would be apparent to those skilled in the art that many more modifications are possible without departing from the inventive concepts herein. The invention, therefore, is not to be restricted except in the spirit of the appended claims.

What is claimed is:

1. An ablation catheter comprising:

an elongated catheter body having proximal and distal ends and a lumen therethrough;

a catheter tip section at the distal end of the catheter body having a lumen extending through at least a portion of the catheter tip in communication with the lumen of the catheter body;

an electrode mounted on the catheter tip section; and a conductive lead extending from the electrode and through the lumens of the catheter body and catheter tip section, said lead comprising a first wire of a first high conductivity material and a second wire of a second high strength material different from the first material non-conductively bonded to the first wire, wherein each of the first and second wires are electrically bonded to an internal surface of the electrode.

2. An ablation catheter as claimed in claim 1 where the first material is copper.

3. An ablation catheter as claimed in claim 1 wherein the second material is constantan.

4. An ablation catheter as claimed in claim 1 wherein the first material is copper and the second material is constantan.

5. An ablation catheter as claimed in claim 1 wherein the electrode is made of a gold alloy.

6. An ablation catheter as claimed in claim 5 wherein the electrode is a ring electrode and the thickness of the electrode is about 0.008 inches.

7. An ablation catheter as claimed in claim 1 comprising at least two electrodes mounted on the catheter tip section.

8. An ablation catheter as claimed in claim 7 wherein the electrodes are spaced apart a distance of from about 2 to about 5 mm.

9. An ablation catheter as claimed in claim 7 wherein the electrodes are spaced apart a distance of from about 3 to about 4 mm.

10. An ablation catheter according to claim 1, wherein the first wire of the conductive lead is electrically connected, either directly or indirectly, to both an RF energy source and to a temperature monitor.

11. A deflectable ablation catheter comprising:

an elongated catheter body having proximal and distal ends and a lumen therethrough;

a catheter tip section at the distal end of the catheter body having an outer wall and first and second off-axis lumens extending through at least a portion of the catheter tip and being separated from each other by a wall, both first and second lumens being in communication with the lumen of the catheter body;

an electrode mounted on the catheter tip section;

a conductive lead extending from the electrode and through the lumen of the catheter body and the first lumen of the catheter tip section, said lead comprising a first wire of a first, high conductivity material and a second wire of a second, high strength material different from the first material from the first material non-conductively bonded to the first wire, wherein each of the first and second wires are electrically bonded to an inside surface of the electrode;

a puller wire extending through the lumen of the catheter body and the second lumen of the catheter tip section, said puller wire being fixedly attached at its distal end to the catheter tip section adjacent the distal end of the catheter tip section; and means for moving the puller wire longitudinally relative to the catheter body to thereby cause deflection of the tip section.

12. A deflectable ablation catheter as claimed in claim 11 wherein the first material is copper.

13. A deflectable ablation catheter as claimed in claim 11 wherein the second material is constantan.

14. A deflectable ablation catheter as claimed in claim 11 wherein in the first material is copper and the second material is constantan.

15. A deflectable ablation catheter as claimed in claim 11 wherein the electrode is made of a gold alloy.

16. A deflectable ablation catheter as claimed in claim 15 wherein the electrode is a ring electrode and the thickness of the ring electrode is about 0.008 inches.

17. A deflectable ablation catheter as claimed in claim 11 comprising at least two electrodes mounted on the catheter tip section.

18. A deflectable ablation catheter as claimed in claim 17 wherein the electrodes are spaced apart a distance of from about 2 to about 5 mm.

19. A deflectable ablation catheter as claimed in claim 17 wherein the electrodes are spaced apart at a distance of from about 3 to about 4 mm.

20. A deflectable ablation catheter as claimed in claim 11 wherein the lead in the first lumen of the catheter tip section extends through the outer wall of the catheter tip section at a location adjacent the first lumen to reach the electrode.

21. An ablation catheter as claimed in claim 11 wherein the lead extending through the first lumen of the catheter tip section extends through the wall of the catheter tip section lying between the first and second lumens and through the outer wall of the catheter tip section adjacent the second lumen to reach the electrode.

22. A deflectable ablation catheter according to claim 11, wherein the first wire of the conductive lead is electrically connected, either directly or indirectly, to both an RF energy source and to a temperature monitor.

23. A system for creating linear lesions in the endocardium by ablation comprising:

an ablation catheter comprising:

an elongated catheter body having proximal and distal ends and a lumen therethrough;

a catheter tip section at the distal end of the catheter body having a lumen extending through at least a portion of the catheter tip in communication with the lumen of the catheter body;

a plurality of electrodes mounted on the catheter tip section; and an electrode lead extending from each electrode through the lumens of the catheter tip section to the proximal end of the catheter body, each of said leads comprising a first wire of a first material and a second wire of a second material different from the first material, said second wire being non-conductively bonded to the first wire, each wire being electrically connected to the electrode;

an ECG monitor;

a source of RF energy comprising at least one RF energy lead;

a temperature monitor; and a switching unit electrically connected to each of the wires of the electrode leads, to at least one RF energy lead, to the temperature monitor and to the ECG monitor, said switching unit comprising means for switching between a first mode wherein an electrical connection is established between the ECG monitor and the electrode leads and a second mode wherein an electrical connection is established between one RF energy lead and a selected electrode lead and simultaneously an electrical connection is made between the temperature monitoring means and the selected electrode lead.

24. A system as claimed in claim 23 further comprising a second means for monitoring temperature and wherein, in the second mode, an electrical connection is established between a second RF energy lead and a second selected electrode lead and an electrical connection is further established between the second temperature monitoring means and the second selected electrode lead.

* * * * *